United States Patent [19]
Haarer et al.

[11] Patent Number: 6,153,389
[45] Date of Patent: Nov. 28, 2000

[54] DNA ADDITIVES AS A MECHANISM FOR UNAMBIGUOUSLY MARKING BIOLOGICAL SAMPLES

[76] Inventors: Brian K. Haarer, 8008 Greenslope Dr., Austin; Nigel S. Atkinson, 500 Peterson St., Round Rock, both of Tex. 78759

[21] Appl. No.: 09/253,788

[22] Filed: Feb. 22, 1999

[51] Int. Cl.[7] .............................. C12Q 1/68; C12P 19/34
[52] U.S. Cl. ......................... 435/6; 435/91.1; 435/91.2; 436/94
[58] Field of Search ........................... 435/6, 91.1, 91.2; 436/94

[56] References Cited

U.S. PATENT DOCUMENTS

| | | | |
|---|---|---|---|
| 4,509,534 | 4/1985 | Tassin, Jr. | 128/764 |
| 4,683,195 | 7/1987 | Mullis et al. | 435/6 |
| 4,683,202 | 7/1987 | Mullis et al. | 435/91 |
| 4,800,159 | 1/1989 | Mullis et al. | 435/172.3 |
| 4,963,663 | 10/1990 | White et al. | 536/27 |
| 5,297,561 | 3/1994 | Hulon | 128/764 |
| 5,316,908 | 5/1994 | Carlson et al. | 435/6 |
| 5,378,602 | 1/1995 | Polymeropoulos et al. | 435/6 |
| 5,451,505 | 9/1995 | Dollinger | 435/6 |
| 5,464,945 | 11/1995 | Reynolds et al. | 435/6 |
| 5,468,610 | 11/1995 | Polymeropoulos et al. | 435/6 |
| 5,514,547 | 5/1996 | Balazs et al. | 435/6 |
| 5,599,666 | 2/1997 | Schumm et al. | 435/6 |
| 5,610,028 | 3/1997 | Frischer et al. | 435/29 |
| 5,643,728 | 7/1997 | Slater et al. | 435/6 |
| 5,665,538 | 9/1997 | Slater et al. | 435/6 |
| 5,674,686 | 10/1997 | Shumm et al. | 435/6 |
| 5,683,896 | 11/1997 | Hartley et al. | 435/91 |
| 5,714,326 | 2/1998 | Dawson | 435/6 |

OTHER PUBLICATIONS

Mullis, et. al., "Specific Enzymatic Amplification of DNA In Vitro: The Polymerase Chain Reaction," Cold Spring Harbor Symposia in Quantitative Biology, vol. L1, pp. 263–273 (1986).
Mullis, et. al., "Specifice Systhesis of DNA in Vitro via a Polymerase–Catalyzed Chain Reaction," Methods in Enzymology, vol. 155, pp. 335–351 (1987).
Saiki, et. al., "Primer–Directed Enzymatic Amplification of DNA with a Thermostable DNA Ploymerase," Reports, Jan. 20, 1988, pp. 487–491 (1988).
Erlich, et. al., "Specific DNA Amplification," Nature, vol. 331, Feb.4, 1988, pp. 461–462 (1988).
"Multiplying Genes by Leaps and Bounds," Research News, vol. 240, Jun. 10, 1988 pp 1408–1410 (1988).
Oste, "Polymerase Chain Reaction," BioTechniques, vol. 6, No. 2, pp 162–167 (1988).
Vosberg "The Polymerase Chain Reaction: An Improved Method for the Analysis of Nucleic Acids," Human Genetics, vol. 83, pp.1–15 (1989).
Kwok, et. al., "Avoiding False Positives with PCR," Nature, vol. 339, May 18, 1989, pp. 237–238 (1989).
Ali, et. al., "DNA Finger Printing by Oligonucleotide Probes Specific for Simple Repeats," Human Genetics, vol. 74, pp. 239–243 (1986).
Waye, "A Simple and Sensitive Method for Quantifying Human Genomic CNA in Forensic Specimen Extracts," BoiTechniques, vol. 7, No. 8, pp.852–855 (1989).
Nakamura, et. al., "Variable Number of Tandem Repeat (VNTR) Markers for Human Gene Mapping," Science, vol. 235, pp.1616–1622 (1987).
Roy, et. al., "Infrared Fluorescent Detection of D1S80 Alleles form Blood and Body Fluid Collected on IsoCode™ Devices," BioTechniques, vol. 23, No. 5, pp.942–945(1997).
Ricciardone, et. al., "Multiplex Systems for the Amplification of Short Tandem Repeat Loci: Evaluation of Laser Fluorescence Detection," BioTechniques, vol. 23, No.4, pp.742747 (1997).
Botstein, et. al., "Construction of a Genetic Linkage Map in Man Using Restriction Fragment Length Polymorphisms," American Journal of Human Genetics, vol. 32 pp.314–331 (1980).
Gill, et. al., "Forensic Application of DNA 'Fingerprints'," Nature, vol. 318, pp.577–579 (1985).
Jeffreys, et. al., "Individual–Specific 'Fingerprints'of Human DNA," Nature, vol. 316, pp. 76–79 (1985).

*Primary Examiner*—Kenneth R. Horlick
*Attorney, Agent, or Firm*—Gianna Julian-Arnold; Pepper Hamilton LLP

[57] ABSTRACT

The present invention is directed to a mechanism for marking biological samples (blood, semen, saliva, etc.) that are to be used for subsequent nucleic acid analysis. The method involves adding a nucleic acid (DNA) molecule of known sequence to the biological sample at the time of sample collection. The method further utilizes primers specific to the complementary strands of the added DNA, such that they will direct the synthesis of another DNA molecule of known length when used in a standard or multiplex polymerase chain reaction (PCR). This provides an unambiguous identifying label for the collected forensic or medical samples, including blood, semen, saliva, urine, tissue, and mixtures of bodily fluids. When used with the supplied primers or DNA probe(s), PCR or nucleic acid hybridization techniques will produce or recognize DNA fragments of predetermined size(s), preventing errant confusion of said samples with other forensic or medical samples that do not contain the aforementioned DNA additive.

18 Claims, 2 Drawing Sheets

DNA ADDITIVES AS A MECHANISM FOR UNAMBIGUOUSLY MARKING BIOLOGICAL SAMPLES

FIELD OF THE INVENTION

The present invention relates generally to the forensic or medical analysis of biological samples. More specifically, the present invention relates to the marking of biological samples for their subsequent distinction from unmarked biological samples in standard forensic nucleic acid analysis.

BACKGROUND OF THE INVENTION

In certain criminal investigations, "known" biological samples (primarily blood, saliva, and semen) are collected from victims, suspects, and their relatives. In these criminal investigations, "unknown" biological specimens are also collected, generally from the crime scene and from residences, automobiles, and other items associated with one or more suspects in the investigation. These unknown biological specimens are often scrapings of drops of blood, saliva, semen, or small tissue fragments.

Both known and unknown biological specimens are subjected to various analyses, including characterizations of their constituent deoxyribonucleic acid (DNA). The standard analysis methods used are (a) analysis of *Variable Numbers of Tandem Repeats* (*VNTR*), (b) analysis of *Short Tandem Repeats* (*STR*), (c) analysis of Single Nucleotide Polymorphisms (SNP), (d) analysis of *Restriction Fragment Length Polymorphisms* (*RFLPs*), and (e) analysis of mitochondrial DNA sequences. VNTR and STR analyses utilize simple or multiplex *Polymerase Chain Reaction* (*PCR*) technology; RFLP analysis utilizes restriction enzyme digestion of DNA followed by DNA hybridization techniques with labeled DNA probes; and mitochondrial DNA sequence analysis utilizes a combination of PCR technology and conventional dideoxy ("Sanger") sequencing in a process known as cycle sequencing.

Results from the above analyses are used to compare the known and unknown samples to determine any possible relationships between the samples.

However, problems may arise due to the deliberate or inadvertent contamination of unknown biological samples by previously collected known biological samples, or by subsequent samples due to the confusion of samples (e.g. during analysis). In the example of criminal forensic analysis, such contamination could arise when blood from a victim is collected at a particular location, then transported to the residence of a suspect and subsequently released at the suspect's residence.

Thus a need exists for a mechanism whereby collected known biological samples would be unambiguously marked and identified at the time of collection. Then, if a marked sample should happen to contaminate another locale, the sample would be recognized as a contaminant upon subsequent analysis. This would also safeguard against the confusion of samples during analysis, preventing a "known" sample from being mistaken as a sample collected from a crime scene.

SUMMARY OF THE INVENTION

It is therefore an object of the present invention to prevent confusion of known forensic or other biological samples with unknown samples, by adding a DNA molecule of defined composition to the known sample at the time of sample collection.

It is a further object of the present invention to have the added DNA molecule be detectable through standard methods of forensic analysis, without interfering with, or confusing the results of, such methods of analysis.

It is a further object of the present invention to decrease, if not eliminate, the possibility that collected biological samples could subsequently serve to contaminate some other person, place, or thing without being detected as an obvious contaminant.

It is a further object of the present invention to provide confirmation that known and unknown samples have not been confused during analysis, and to provide instant notification if such confusion does take place.

It is a further object of the present invention to improve the integrity of the data, such that analysis results are more likely to hold up in court.

It is a further object of the present invention to provide a marker for the known samples that shows up during the course of forensic analysis, and therefore does not require special detection methods beyond the inclusion of appropriate DNA primers or hybridization probes, depending on the method of analysis.

The present invention accomplishes the above and other objectives by providing a mechanism for marking biological samples (blood, semen, saliva, etc.) that are to be used for subsequent nucleic acid analysis. The method involves adding a nucleic acid (DNA) molecule of known sequence to the biological sample at the time of sample collection. The method further utilizes primers specific to the complementary strands of the added DNA such that they will direct the synthesis of another DNA molecule of known length when used in a standard or multiplex polymerase chain reaction (PCR). This provides an unambiguous identifying label for the collected forensic or medical samples, including blood, semen, saliva, urine, tissue, and mixtures of bodily fluids. When used with the supplied primers or DNA probe(s), PCR or nucleic acid hybridization techniques will produce or recognize DNA fragments of predetermined size(s), preventing errant confusion of said samples with other forensic or medical samples that do not contain the aforementioned DNA additive.

BRIEF DESCRIPTION OF THE DRAWINGS

FIG. 2A illustrates a single template used with two alternative sets of primers.

FIG. 2B illustrates two templates used with a single set of primers.

FIG. 2C illustrates two templates used with two alternative sets of primers.

DETAILED DESCRIPTION OF THE INVENTION

Figure 1:
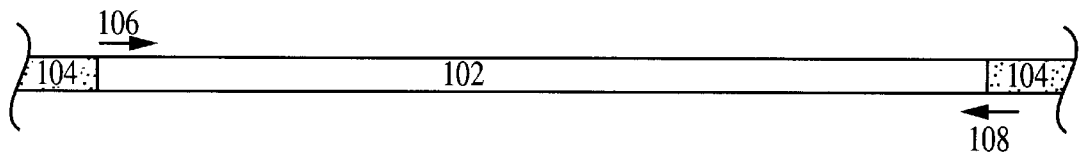
FIG. 1 illustrates the basic DNA additive and single primer set.

The present invention is a process whereby a defined and unique marker DNA is added to biological samples collected from known individuals by standard methods. Such tagging of collected samples effectively prevents their subsequent confusion with samples ("unknowns") that do not contain the defined marker DNA. Examples of unknown biological samples would be those collected at crime scenes or from crime victims, including but not limited to blood scrapings, hair, semen, saliva, blood, tissue scrapings, urine, mixtures of body fluids, etc.

The present invention is consistent with commonly used techniques for forensic analysis. These include Short Tandem Repeat (STR), Variable Number of Tandem Repeats (VNTR), Single Nucleotide Polymorphisms (SNP), Restriction Fragment Length Polymorphism (RFLP), and mitochondrial sequencing analysis methods. These techniques are well known to those skilled in the art, and are described in the following references, each of which is incorporated herein by reference in its entirety.

(i) General reference for RFLP, VNTR, STR, and mitochondrial sequencing (the second reference also includes SNP, though not by that name):

Lincoln, P. J., and J. Thomson, eds. 1998. Forensic DNA Profiling Protocols. Humana Press, Inc.

Landegren, U., R. Kaiser, C. T. Caskey, and L. Hood. 1988. DNA diagnostics—molecular techniques and automation. Science. 242:229–237.

(ii) RFLP analysis:

Botstein, D., R. L. White, M. Skolnick, R. W. Davis. 1980. Construction of a genetic linkage map in man using restriction fragment length polymorphisms. Am. J. Hum. Genet. 32:314–331.

(iii) VNTR analysis:

Nakamura et al. 1987. Variable number of tandem repeat (VNTR) markers for human gene mapping. Science. 235:1616–1622.

(iv) STR analysis:

Edwards, A., A. Civitello, H. A. Hammond, and C. T. Caskey. 1991. DNA typing and genetic mapping with trimeric and tetrameric tandem repeats. Am. J. Hum. Genet. 49:746–756.

Ricciardone et al. 1997. Multiplex systems for the amplification of short tandem repeat loci: evaluation of laser fluorescence detection. Biotechniques. 23:742–747.

(v) SNP analysis:

Nickerson, D. A., R. Kaiser, S. Lappin, J. Stewart, L. Hood, and U. Landegren. 1990.

Automated DNA diagnostics using an ELISA-based oligonucleotide ligation assay.

Proc. Natl. Acad. Sci. USA. 87:8923–8927.

Nikiforov, T. T., R. B. Rendle, P. Goelet, Y. H. Rogers, M. G. Kotewicz, S. Anderson, G. L. Trainor, and M. R. Knapp. 1994. Genetic bit analysis: a solid phase method for typing single nucleotide polymorphism. Nucleic Acids Res. 22:4167–4175.

Ross, P. L., K. Lee, and P. Belgrader. 1997. Discrimination of single-nucleotide polymorphisms in human DNA using peptide nucleic acid probes detected by MALDI-TOP mass spectrometry. Anal. Chem. 69:4197–4202.

(vi) General PCR analysis:

Mullis et al. 1986. Specific enzyme amplification of DNA in vitro: the polymerase chain reaction. Cold Spring Harbor Symp Quant. Biol. 51:263–273.

Mullis, K. B., D. H. Gelfand, S. Stoffel, S. J. Scharf, R. Higuchi, G. T. Horn GT, K. B. Mullis, and H. A. Erlich HA. 1988. Primer-directed enzymatic amplification on DNA with thermostable DNA polymerase. Science 239:487–491.

In a preferred embodiment of the present invention, the DNA additive is introduced irreversibly into the known samples at the time of collection. This can be accomplished by providing the DNA additive in the most commonly used collection vessels, including vacutainer tubes, FTA Blood Stain Collection Cards™ (or similar blood collection and preservation systems), saliva collection swabs, etc.

The present invention comprises a fragment or fragments of DNA of known sequence that are introduced into known samples. The DNA is provided either as an insert within a plasmid host that allows amplification in E. coli, or is added as a linear fragment. The length of the DNA(s) is such that it/they (a) provide PCR product(s) of known lengths when used with appropriate oligonucleotide primers in a PCR reaction in conjunction with either STR or VNTR analysis, (b) provide restriction fragments of known lengths that can be detected with defined nucleic acid probes when used in RFLP analysis, and (c) generate a unique known DNA sequence when used with the appropriate oligonucleotide sequencing primer(s) in conjunction with mitochondrial sequencing (in cycle sequencing reactions).

Figure 2A:
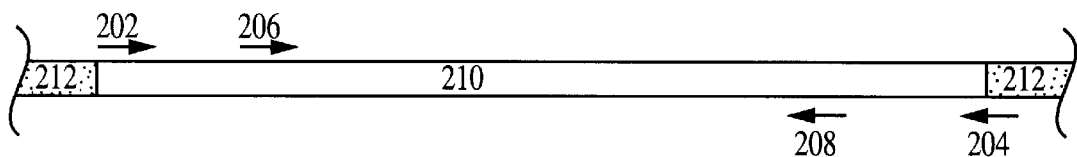
FIGS. 2A–2C illustrate alternative methods for generating two distinct fragments from PCR reactions(s).
Figure 2B:
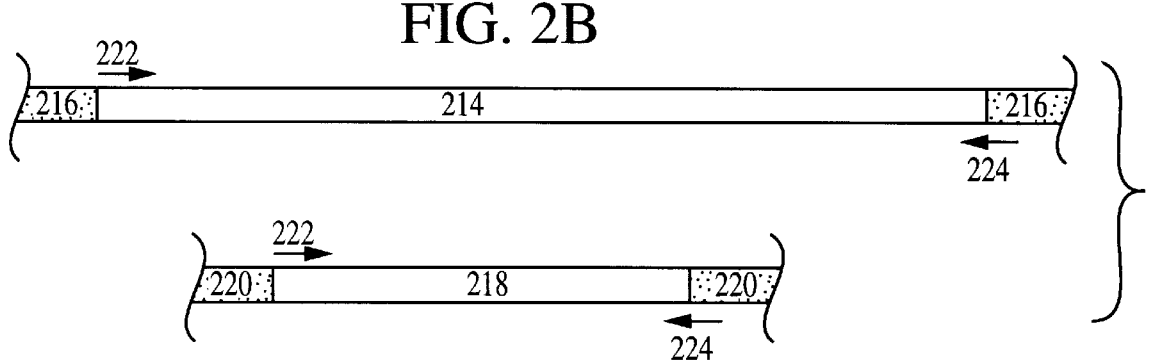
Figure 2C:
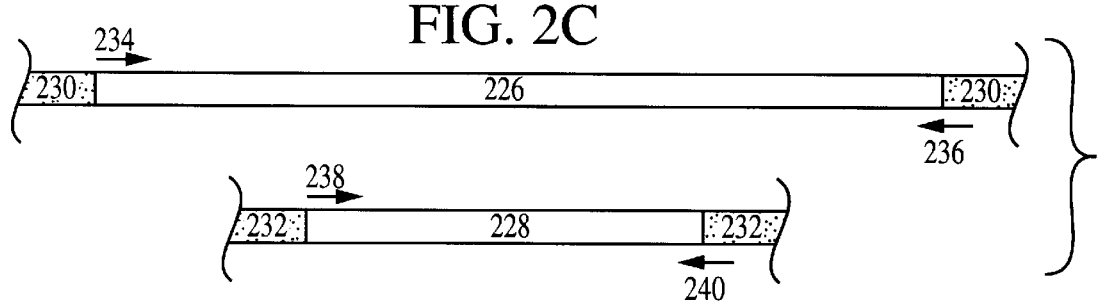
Figure 3:
FIG. 3 illustrates restriction sites at ends of DNA additive for use with RFLP analysis.

Variations on the exact nature of the added DNA are shown in FIGS. 1–3. FIG. 1 illustrates the basic form of the DNA additive, where the DNA fragment of known length and sequence is used in conjunction with primers complementary to its two ends, such that a PCR reaction utilizing these three components (DNA additive and two primers) will produce a PCR product of defined length. This length should be of similar size to products generated by standard STR or VNTR primer sets. The DNA additive consists of DNA fragment of known sequence 102 inserted into a plasmid vector, (portions of the plasmid vector adjacent to the insert are shown 104). A single primer set consists of first PCR primer 106 and second PCR primer 108 which are used to identify the presence of the DNA additive. In the PCR, first PCR primer 106 and second PCR primer 108 amplify, from the DNA additive, a DNA fragment of known size and sequence.

Since STR and VNTR analyses differ in the size range of PCR products generated, it may be necessary to develop DNA additives that are capable of generating at least two sizes of PCR products. This can be accomplished by one of the methods illustrated in FIGS. 2A–2C.

FIG. 2A illustrates a single DNA additive that has binding sites for two different primer sets; the primer set used is determined by the type of forensic analysis being performed. First primer set is shown as first primer 202 and second primer 204. Second primer set is shown as third primer 206 and fourth primer 208. A DNA fragment of known sequence 210 is inserted into a plasmid vector, (portions of the plasmid vector adjacent to the insert are shown 212). For example, the first primer 202 and second primer 204 would be used in a PCR reaction with the DNA additive to generate a DNA fragment of a size consistent with VNTR analysis, while the third primer 206 and fourth primer 208 would be used in a separate PCR reaction with the DNA additive to generate a DNA fragment of a size consistent with STR analysis, which examines smaller DNA fragments than does VNTR analysis.

FIG. 2B illustrates a means by which two distinct DNA additives could be provided with a single primer set. Here, first DNA fragment of known sequence 214 is inserted into a plasmid vector, (portions of the plasmid vector adjacent to the insert are shown 216) and second DNA fragment of known sequence 218 is inserted into a plasmid vector, (portions of the plasmid vector adjacent to the insert are also shown 220). The primer set consists of first primer 222 and second primer 224. In this situation, use of first primer 222 and second primer 224 in PCR reactions simultaneously on the two DNA additives would generate DNA fragments consistent with multiple methods of analysis. PCR from template 214 would generate a DNA fragment consistent with methods such as VNTR, that analyze longer DNA fragments, and PCR from template 218 would generate a DNA fragment consistent with methods such as STR, that analyze shorter DNA fragments.

FIG. 2C illustrates a means by which two distinct DNA additives could be provided with two distinct primer sets. Here, two templates are used with two alternative sets of primers. A first DNA fragment of known sequence 226 and a second DNA fragment of known sequence 228 are each inserted into a plasmid vector, (portions of the plasmid vector adjacent to the first insert 230 and the second insert 232 are shown). First primer set is shown as first primer 234 and second primer 236. Second primer set is shown as third primer 238 and fourth primer 240.

The DNA additives in FIGS. 2A and 2C are compatible with DNA sequencing methods as shown; the additive of FIG. 2B is only compatible when an additional unique set of primers specific for one of the two added DNA molecules is used for the DNA sequence analysis.

FIG. 3 illustrates the necessary features for use of the DNA additive in RFLP analysis; this design can easily be incorporated into any of the additive methods described in FIGS. 2A–2C. Known restriction enzyme site(s) are engineered at or near the ends of the DNA insert, and are used to release a DNA fragment of known length and sequence from the DNA additive. Enzyme one 302 and enzyme two 304 can represent the same or different restriction enzyme recognition sequences, and can represent single or multiple known restriction enzyme recognition sequences.

In a preferred embodiment, the DNA additive comprises one or more of the following features:

(a) the added DNA is stable for a length of time comparable to the shelf life of collected biological specimens;

(b) the added DNA and any primers used in conjunction with the added DNA do not interfere with the chosen form of analysis, and do not produce any PCR products, restriction fragments, bands detected by hybridization analysis, or DNA sequence other than expected for the added DNA. This requirement holds for the effects of oligonucleotide primers specific to the added DNA on DNA from the known biological sample, and for the effects of oligonucleotide primers normally used in forensic analysis methods on the DNA additive.

(c) the added DNA is compatible with, and stable through, standard DNA preparation procedures specific for the type of collection vessel and for the specific forensic analysis protocol used;

(d) the concentration of the added DNA is such that it will be present in molar ratios similar to those of analysis targets in the known biological sample after preparation of the sample for analysis; and (e) the DNA additive, or products generated from the DNA additive (e.g. by PCR), is compatible with commonly used methodologies for the subsequent analysis of such products, including, but not limited to: DNA hybridization analysis, agarose gel electrophoresis, polyacrylamide gel electrophoresis, capillary electrophoresis, and matrix-assisted laser desorption ionization time-of-flight (MALDI-TOF) mass spectrometry.

In practice, the present invention comprises adding a nucleic acid of known sequence to standard collection vessels for forensic and medical biological samples; collecting the biological samples in the collection vessel containing the known nucleic acid additive; extracting the DNA from the biological sample; providing nucleic acid primers complementary to the known nucleic acid additive and analyzing the extracted DNA using standard assay techniques in conjunction with the provided primers. Standard assay techniques are known to those skilled in the art and include but are not limited to PCR-based analysis of short tandem repeats; PCR-based analysis of variable numbers of tandem repeats; DNA hybridization analysis of restriction fragment length polymorphisms; and the sequencing of mitochondrial DNA. In alternative embodiments the method can comprise: 1/ the use of a single primer set with a single DNA additive to produce a PCR product of defined length; 2/ the use of multiple primer sets with a single DNA additive to produce fragments of different sizes in separate PCR reactions, 3/ a single primer set used with multiple DNA additives to produce multiple fragments in a PCR reaction, and/or 4/ multiple primer sets used with multiple DNA additives to produce multiple fragments in a PCR reaction.

To support the process of the present invention, oligonucleotide primers or DNA hybridization probes necessary for the appropriate detection of the added DNA could be supplied either independently or as components of commonly used assay kits.

In practice, it is preferred that oligonucleotide primers or DNA hybridization probes used for the detection of the DNA additive are used on all samples analyzed, regardless of whether they contain the DNA additive. Therefore, it is advantageous to supply necessary primers as standard components in STR and VNTR PCR reactions, Further, it is preferred that (cycle) sequencing using primers specific for the DNA additive be performed on all samples being analyzed for mitochondrial DNA sequence. Finally, it is preferred that DNA hybridization probes specific for the DNA additive be used to probe all samples being tested by RFLP analysis.

Any given set of PCR primers might support amplification of a DNA fragment from the genomes of a small percentage of the population that had not been identified during the design and testing of the DNA additive. This could give rise to false positives. In practice, this does not present much of a problem since the spuriously amplified fragment will most likely be a different size than a fragment amplified from the DNA additive. Furthermore, DNA sequence analysis could be used to confirm that the fragment arose as a result of amplification from the DNA additive.

In a preferred embodiment, the additive will be designed so that it contains binding sites for more than two PCR primers, thereby providing a simpler method to prevent the production of false positives. In this case, the presence of the DNA additive can be confirmed by performing multiple PCR reactions, each using a different set of primers. Each PCR reaction would generate an amplification product of known size and sequence from the DNA additive. Samples that contain the DNA additive would produce positive PCR reactions with all of the primer sets. The ability to confirm the presence of the additive by multiplex PCR greatly increases the robustness of the procedure.

In an alternative embodiment, different DNA additives are used for different individuals to provide further protection against mislabeling the samples. Here, if the DNA additive which was to have been used for Jane Doe is found in the sample labeled John Smith, then additional sampling of the possibly misidentified individuals would be indicated.

Having thus described the basic concept of the invention, it will be readily apparent to those skilled in the art that the foregoing detailed disclosure is intended to be presented by way of example only, and is not limiting. Various alterations, improvements and modifications will occur and are intended to those skilled in the art, but are not expressly stated herein. These modifications, alterations and improvements are intended to be suggested hereby, and within the scope of the invention. Accordingly, the invention is limited only by the following claims and equivalents thereto.

What is claimed is:

1. A process for marking biological samples used in subsequent nucleic acid analysis comprising:
   collecting at least one known biological sample;
   introducing at least one fragment of deoxyribonucleic acid (DNA) of known length and sequence into the known biological sample wherein said DNA fragment tags or marks the biological sample, and wherein said DNA fragment does not interfere with subsequent nucleic acid analysis of the biological sample.

2. The process for marking biological samples used in subsequent nucleic acid analysis of claim 1, wherein introducing at least one fragment of DNA further comprises:
   providing the DNA fragment as an insert within a plasmid host.

3. The process for marking biological samples used in subsequent nucleic acid analysis of claim 1, wherein introducing at least one fragment of DNA further comprises:
   providing the DNA fragment as a linear fragment.

4. The process for marking biological samples used in subsequent nucleic acid analysis of claim 1, wherein introducing at least one fragment of DNA further comprises:
   inserting the DNA fragment into a plasmid vector.

5. The process for marking biological samples used in subsequent nucleic acid analysis of claim 4, further comprising:
   identifying the DNA fragment through the presence of a first polymerase chain reaction primer and a second polymerase chain reaction primer.

6. The process for marking biological samples used in subsequent nucleic acid analysis of claim 1, wherein the known length of the DNA fragment is (1) a length of DNA which provides PCR product(s) of known lengths when used with appropriate oligonucletide primers, in a PCR reaction in conjunction with short tandem repeats analysis, (2) a length of DNA which provides PCR product(s) of known lengths when used with appropriate oligonucletide primers, in a PCR reaction in conjunction with variable numbers of tandem repeats analysis, (3) a length of DNA which can be detected with defined nucleic acid probes when used in restriction fragment length polymorphisms, or (4) a length of DNA which generates a unique known DNA sequence when used with the appropriate oligonucleotide sequencing primer(s) with mitochondrial sequencing.

7. The process for marking biological samples used in subsequent nucleic acid analysis of claim 6 further comprising:
   administering to the DNA fragment primers complementary to its two ends.

8. The process for marking biological samples used in subsequent nucleic acid analysis of claim 6 wherein the DNA fragment has binding sites for two different primers.

9. The process for marking biological samples used in subsequent nucleic acid analysis of claim 6 wherein a first DNA fragment is inserted into a first plasmid vector and a second DNA fragment is inserted into a second plasmid vector.

10. The process for marking biological samples used in subsequent nucleic acid analysis of claim 9, wherein the first DNA fragment and the second DNA fragment each have binding sites for two different primers.

11. The process for marking biological samples used in subsequent nucleic acid analysis of claim 6, wherein the DNA fragment has at least one attribute selected from the group consisting of (1) the DNA fragment has a stability comparable to the stability of the biological sample, (2) the DNA fragment in conjunction with primers used in the addition thereof does not interfere with the subsequent analysis of the known biological sample, (3) the DNA fragment in conjunction with primers used in the addition thereof does not produce any polymerase chain reaction products, restriction fragments, bands detected by hybridization analysis, or DNA sequence other than expected for the added DNA fragment, (4) the DNA fragment is compatible with, and stable through, standard DNA preparation procedures, (5) the concentration of the DNA fragment is of a predetermined amount such that it will be present in molar ratios similar to those of the analysis targets in the known biological samples after preparation of the sample for analysis and (6) the DNA fragment, or products generated from the DNA fragment, is compatible with at least one of DNA hybridization analysis, agarose gel electrophoresis, polyacrylamide gel electrophoresis, capillary electrophoresis, or matrix assisted laser desorption ionization time-of-flight mass spectrometry.

12. The process for marking biological samples used in subsequent nucleic acid analysis of claim 11, wherein the DNA fragment is added to a collection vessel.

13. A process for marking biological samples used in subsequent nucleic acid analysis comprising:
   introducing at least one fragment of deoxyribonucleic acid (DNA) of known length and sequence into a collection vessel;
   collecting at least one known biological sample;
   adding the known biological sample to the collection vessel to obtain a modified biological sample;
   extracting the DNA from the modified sample to obtain extracted DNA;
   providing primers complementary to the extracted DNA to obtain a resulting sample;
   analyzing the resulting sample using a technique selected from the group, consisting of polymerase chain reaction-based analysis of short tandem repeats; polymerase chain reaction-based analysis of variable numbers of tandem repeats; DNA hybridization analysis of restriction fragment length polymorphisms; and the sequencing of mitochondrial DNA.

14. The process for marking biological samples used in subsequent nucleic acid analysis of claim 13, further comprising:
   producing a polymerase chain reaction product of defined length using a single primer set with a single fragment of DNA.

15. The process for marking biological samples used in subsequent nucleic acid analysis of claim 13, further comprising:
   producing fragments of differing sizes in separate polymerase chain reactions using multiple primer sets with a single fragment of DNA.

16. The process for marking biological samples used in subsequent nucleic acid analysis of claim 13, further comprising:

producing multiple fragments in a polymerase chain reaction using a single primer set with multiple DNA fragments.

17. The process for marking biological samples used in subsequent nucleic acid analysis of claim 13, further comprising:

producing multiple fragments in a polymerase chain reaction using multiple primer sets with multiple DNA fragments.

18. The process for marking biological samples used in subsequent nucleic acid analysis of claim 13, wherein the primers are supplied as components of assay kits.

* * * * *